United States Patent
Halbert (10) Patent No.: US 7,341,058 B2
(45) Date of Patent: Mar. 11, 2008

(54) NEONATAL VALVED MANIFOLD

(75) Inventor: Alan P. Halbert, Bluffdale, UT (US)

(73) Assignee: C.R. Bard, Inc., Murray Hill, NJ (US)

( * ) Notice: Subject to any disclaimer, the term of this patent is extended or adjusted under 35 U.S.C. 154(b) by 603 days.

(21) Appl. No.: 10/921,020

(22) Filed: Aug. 17, 2004

(65) Prior Publication Data

US 2006/0037618 A1    Feb. 23, 2006

(51) Int. Cl.
*A61M 15/00* (2006.01)

(52) U.S. Cl. .......................... 128/203.12; 128/207.16; 128/912

(58) Field of Classification Search ........... 128/200.24, 128/200.26, 202.27, 203.12, 205.24, 207.14, 128/207.12, 207.15, 207.16, 909, 912; 604/30, 604/33, 35, 246–250, 290, 905, 171, 205, 604/280, 142, 149, 208; 251/205, 206, 209, 251/217, 320, 322; 137/907, 908
See application file for complete search history.

(56) References Cited

U.S. PATENT DOCUMENTS

| | | | |
|---|---|---|---|
| 3,406,705 A * | 10/1968 | Meyer | .......................... 137/207 |
| 5,140,983 A | 8/1992 | Jinotti | |
| 5,333,607 A | 8/1994 | Kee et al. | |
| 5,354,267 A | 10/1994 | Niermann et al. | |
| 5,357,946 A | 10/1994 | Kee et al. | |
| 5,445,141 A | 8/1995 | Kee et al. | |
| 5,487,381 A | 1/1996 | Jinotti | |
| 5,642,726 A | 7/1997 | Owens et al. | |
| 5,730,123 A | 3/1998 | Lorenzen et al. | |
| 5,735,271 A | 4/1998 | Lorenzen et al. | |
| 5,882,348 A | 3/1999 | Winterton et al. | |
| 6,612,304 B1 * | 9/2003 | Cise et al. | ............. 128/200.26 |
| 6,729,326 B1 | 5/2004 | Winterton et al. | |
| 6,935,339 B2 * | 8/2005 | Mattar Neto et al. | ... 128/207.16 |
| 7,188,623 B2 * | 3/2007 | Anderson et al. | ...... 128/207.16 |
| 2007/0044806 A1 * | 3/2007 | Madsen et al. | ........ 128/207.15 |

FOREIGN PATENT DOCUMENTS

EP     312073 A2 *   4/1989

* cited by examiner

*Primary Examiner*—Justine R. Yu
*Assistant Examiner*—Shumaya B. Ali
(74) *Attorney, Agent, or Firm*—Holland & Hart (57) ABSTRACT

An improved manifold assembly useful in patient ventilation/aspiration systems includes a stop cock valve with a hollow stem and a transverse port arranged to permit the stem to be rotated between open and closed positions. In both positions, a ventilating pathway is maintained through the stem between ventilator and patient connection ports of the manifold. In the open position the stem provides a travel pathway for a catheter between the patient connection port and an access port of the manifold. In the closed condition, the stem seals this travel pathway. The improvement provides an arrangement of structure operable to resist imparting shear damage to an inserted catheter, and to provide enhanced feedback to an attendant, as the stem is manually rotated into contact with the catheter.

30 Claims, 5 Drawing Sheets

NEONATAL VALVED MANIFOLD

BACKGROUND OF THE INVENTION

1. Field of the Invention

This invention relates generally to valved manifold devices of the type used at the patient intubation interface of neonatal endotracheal ventilation/aspiration systems. It is specifically directed to an improved valve stem interface structured to protect against accidental shearing of fragile aspiration catheters positioned within such manifolds.

2. State of the Art

Many gas delivery systems, particularly in a hospital or laboratory environment, utilize manifold devices for directing fluid flow. There is a variety of circumstances in which it is necessary or desirable to provide multiple, yet isolated, other path ways through the interior of such a manifold. The manifold is often associated with other components as a system.

As an example, closed systems for endotracheal suctioning and ventilating typically include a manifold enabling introduction of ventilating gases and intermittent exhalation of patient breath simultaneously with insertion and operation of a tracheal suctioning catheter. The manifold structure typically includes multiple ports, usually the open ends of respective conduits extending from a common chamber. One such port is interfaced to a patient through a patient connection device. The suction catheter is often included within an assembly which is connectable to a second port of the manifold. The catheter assembly conventionally includes a collapsible plastic envelope positioned entirely to surround the catheter. A practitioner manually externally collapses the envelope onto the external surface of the catheter, and advances the catheter through the manifold into an access tube connected to a patient, retracting the catheter in a similar fashion following the aspiration procedure.

The manifold thus provides a first pathway for ventilation gases, and a second pathway for the catheter. The catheter provides isolation from the ventilating gases for fluids withdrawn from the patient through the manifold. When the catheter is withdrawn, it is often desired to continue regulated ventilation through the manifold. In some cases, it is desirable for the catheter assembly to be disconnected from the manifold, without disturbing the ventilation of the patient. It is thus necessary to provide for a gas tight sealing of the pathway formerly occupied by the catheter upon its removal. Early efforts in this connection have involved the provision of auxiliary sealing structures for use in association with the manifold. Eventually, specialized valves were developed for inclusion in a manifold assembly. These valves are structured to provide a travel path for a catheter when catheter suction is needed, while maintaining an adequate seal.

Material prior art structures and methods are described, among other places, in U.S. Pat. No. 5,333,607 to Kee, et al.; U.S. Pat. No. 5,354,267 to Niermann, et al.; U.S. Pat. Nos. 5,357,946 and 5,445,141 to Kee, et al.; U.S. Pat. Nos. 5,140,983 and 5,487,381 to Jinotti; U.S. Pat. No. 5,882,348 to Winterton et al.; U.S. Pat. Nos. 5,735,271 and 5,730,123 to Lorenzen et al. and U.S. Pat. No. 5,642,726 to Owens et al. These patents each disclose ventilator manifold devices and systems in which those devices are utilized. The '267 patent, for example, discloses a manifold and a multi-position stop cock valve. The valve is provided with a "Tee" shaped internal stem channel pattern so that the stem may be positioned selectively to wash the internal lumen of a catheter, to irrigate the patient or to accommodate travel of the catheter through the stem to suction the patient. The valve may be plugged directly into an access port of the manifold. Patient ventilation is conducted without respect to the valve through other ports of the manifold. The valve itself constitutes an integral component of a catheter assembly, and must be removed from the manifold with the remainder of that assembly. The '348 patent discloses a valved manifold embodying a multi-position stop cock valve. The ventilation port is transverse the patient interface port, and is thus characterized by more dead air space than is generally regarded as acceptable for neonatal applications.

U.S. Pat. No. 6,729,326, issued May 4, 2004, to Winterton, et al., discloses an inexpensive, yet reliable, manifold assembly incorporating a valve positioned to minimize dead air space within the manifold and capable of passing a catheter. The assembly includes a valve that provides a sealed gas flow path through the manifold in both its open and closed conditions with respect to catheter travel. The assembly is particularly useful in neonatal applications, because it is constructed to minimize fluid flow turbulence of ventilating gases and to minimize the likelihood of respiratory therapy fluids introduced through an aspiration catheter from back-washing into the ventilation channel of the manifold. The valve component of the assembly is of the stop cock variety. That is, it comprises a stem or core element which is rotated between open and closed conditions within a housing. In both conditions, an open passageway, comprising a portion of the ventilation circuit, exists through the valve stem. In this arrangement, an aspiration catheter must pass through the interface between the valve stem and the inner wall of the housing to enter and pass through the interior of the stem. The disclosure of the '326 patent is incorporated by reference in its entirety as a portion of this disclosure for its teachings concerning the structure and operation of valved manifolds in medical applications.

The aspiration catheters used to aspirate adults or juveniles are sufficiently rugged to resist closure of a valve within which they are positioned. In the event that an operator inadvertently attempts to close the valve, this resistance alerts the attendant, or operator, to the presence of the catheter. Either the catheter can then be removed to permit valve closure, or it is recognized that the catheter should remain in place, and the valve should be left open. Neonatal catheters are relatively fragile, compared to those used for the aspiration of adults or juveniles. While neonatal catheters may be manufactured from similar, or the same, material as catheters for adults, the smaller size of neonatal catheters, and attendant smaller cross-section, renders such catheters more susceptible to damage. In practice, an inadvertent or mistaken effort to close the valve with such a catheter in place can result in severe damage to the catheter. It is conceivable that a distal portion of a neonatal catheter can be completely severed by action of a user closing a valve element, thereby placing an intubated patient at risk of receiving the severed tip as an undesired pulmonary implant.

BRIEF SUMMARY OF THE INVENTION

This invention provides an improvement to valve structures having an interface between two surfaces movable with respect to each other between open and closed conditions. For simplicity, it is described with particular reference to valves having rotating stems within a valve housing, most notably of the type disclosed by the '326 patent. It is described in this disclosure by reference to neonatal ventilation circuits, although it has other uses, particularly in connection with other medical procedures requiring the passage of a delicate tube through a valve.

According to this invention, a recess, which may be regarded as a "pocket," is provided to operate on a portion of an inserted catheter near the interface between the stem and the internal wall surface of the housing. That is, the pocket receives a portion of a catheter passing through a bore communicating through the housing to the interior of the stem. The pocket is structured and arranged such that as the stem is rotated from its open condition towards its closed condition, the attendant will become aware of resistance to valve closure before the catheter is exposed to damaging shear forces. According to certain embodiments, the pocket is structured such that the stem can be rotated to a closed condition without shearing the catheter.

The pocket operates, in part, to change a load condition imposed by the valve components upon the catheter sidewall from an essentially pure applied shear load to a loading condition including a component of force directed along an axis of the catheter, or normal to the shear plane of an applied load on the catheter cross-section. The load condition provided by the invention permits an operator to receive enhanced feedback, compared to the prior art, that the catheter is still in place and must be removed. Furthermore, when undesirably closing a valve onto a catheter, a portion of an applied load on the catheter typically is in a direction operable to separate valve components potentially to provide clearance between sealing members for a squashed catheter.

In certain embodiments, the different loading on a catheter afforded by the instant invention permits seal components to separate sufficiently to resist excessively damaging the catheter, even if the valve accidentally is rotated to a substantially closed position. However, the invention provides enhanced feedback to a user to avoid catheter damage. Furthermore, preferred embodiments virtually eliminate risk of shearing off an end portion of a catheter.

In any case, the configuration of the pocket generally allows a catheter to be flattened and folded between a stem and its housing, rather than sheared into two pieces. In certain embodiments, the pocket can change an end constraint condition caused by at least one valve component (stem and/or housing), to permit rotation and reorientation of a portion of the catheter held by that component. The reoriented catheter portion is more able to bend and fold to avoid shear induced damage. A currently preferred embodiment reduces a shear stress concentration in an area of an entrapped catheter's cross-section.

The term "shear forces" is used in this disclosure in a broad sense to include all of the pressures and forces inherently applied to the catheter at the interface between the stem and housing as the stem is rotated. The term "damaging" refers to the magnitude of shear forces resulting in a catheter's becoming subjectively unfit for continued use, having been subjected to those forces. It is recognized that a catheter may be dented, or visibly impacted, by valve actuation. Such denting in an undamaged catheter sometimes may be massaged by a user to return a catheter to an undented configuration. Alternatively, the dented catheter sidewall may creep back to an undented configuration of its own volition. In any case, a damaged catheter is subjectively unfit for continued use.

BRIEF DESCRIPTION OF THE SEVERAL VIEWS OF THE DRAWINGS

In the drawings, which illustrate what are currently regarded as the best modes for carrying out the invention.

DETAILED DESCRIPTION OF THE INVENTION

Figure 1:
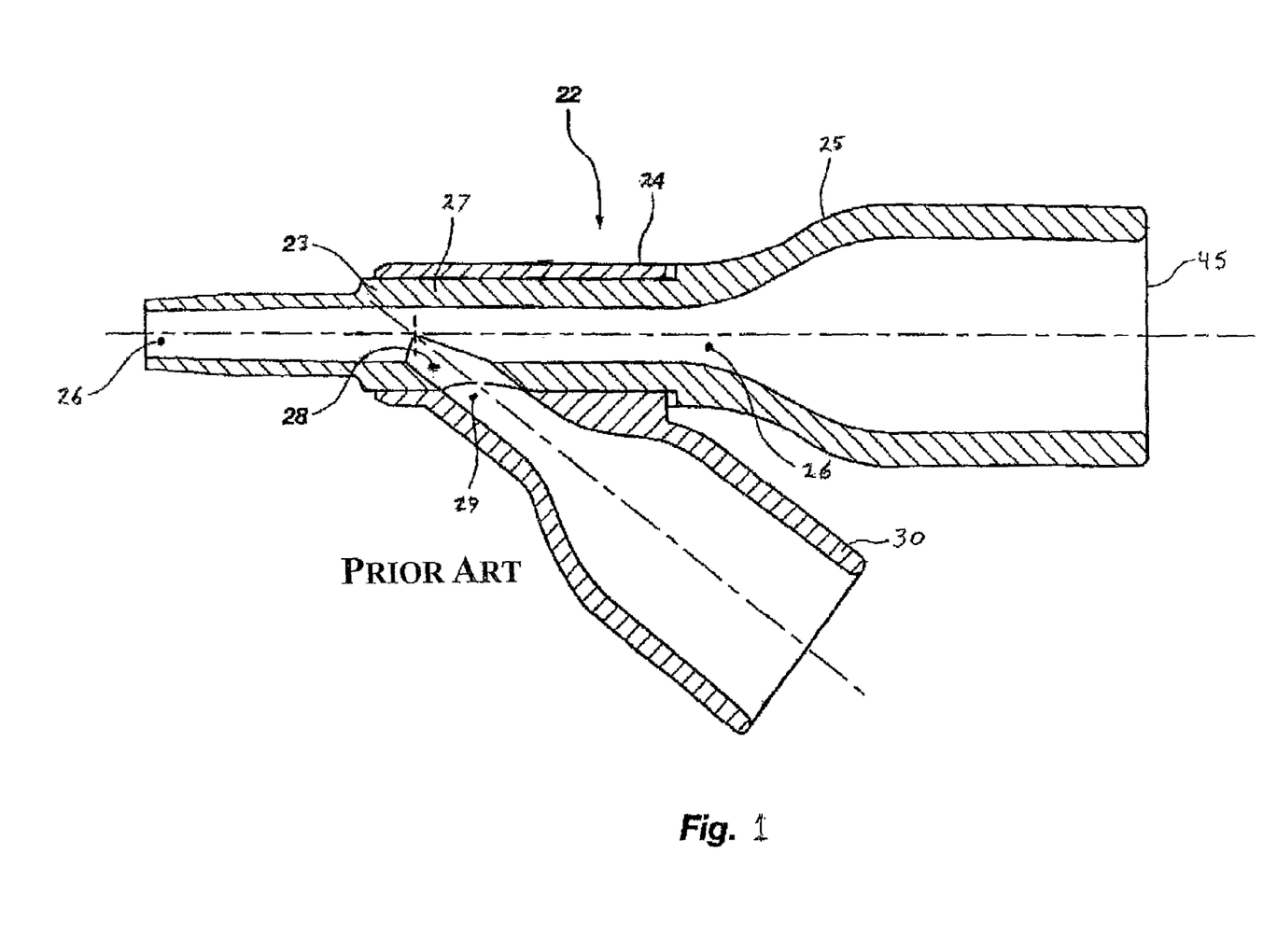
FIG. 1 is a side view in section of a valved manifold portion of a conventional
Figure 2:
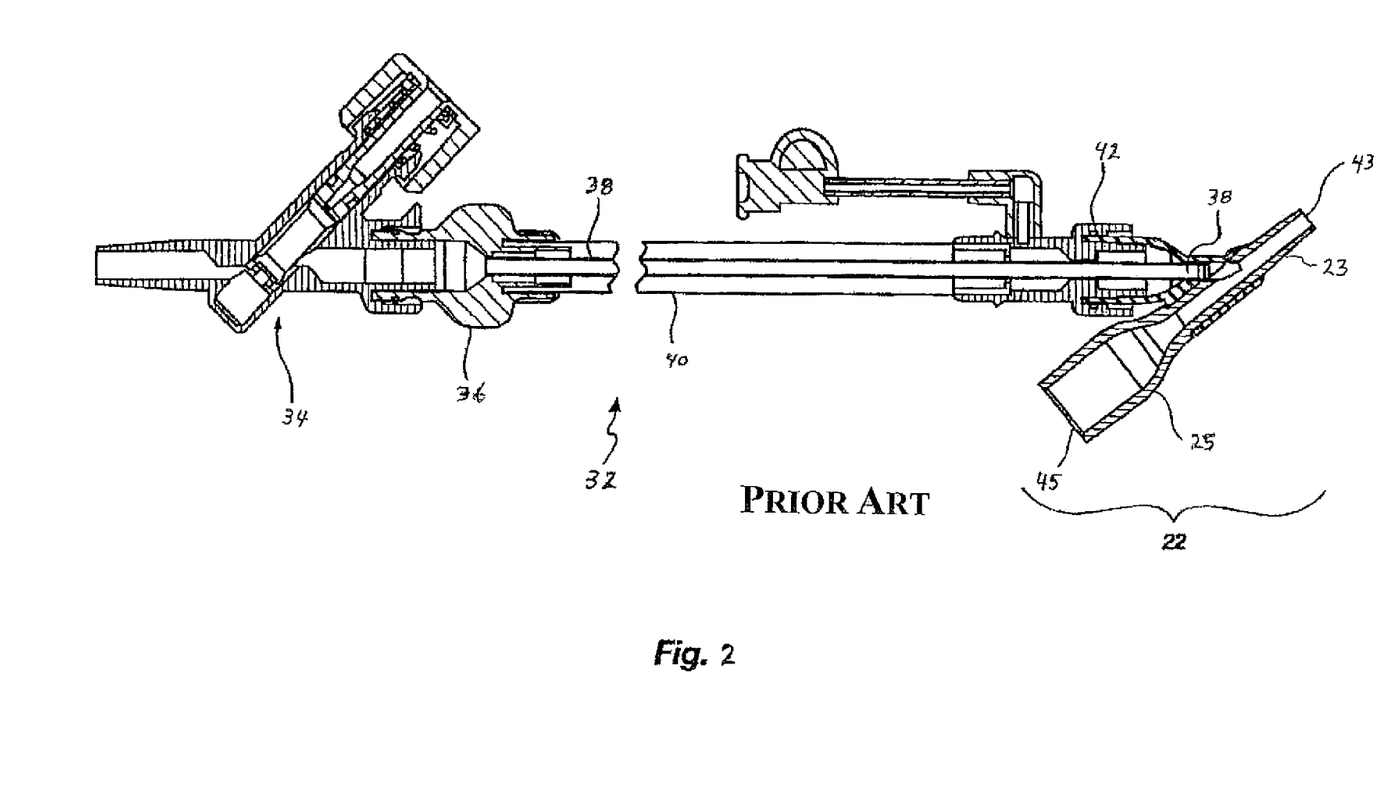
FIG. 2 is a side view in section illustrating the manner in which the valved manifold of FIG. 1 may be connected in operable association with components of a suction catheter assembly.

FIGS. 1 and 2 illustrate certain details of construction of a ventilation/aspiration arrangement of the type disclosed by the '326 patent. The illustrated arrangement includes a valved manifold assembly, designated generally 22, which comprises a stem element 23 configured to mount within a valve housing portion 24. The stem element 23 is integral with a ventilator connection structure 25, which functions as a knob, in that it may be turned by finger pressure to rotate the stem element 23. The stem element 23 is structured with an open interior 26, defined by a continuous wall 27. When the stem element 23 is installed within the valve housing portion 24, the open stem interior 26 provides a passageway for ventilation gasses, among other things. The stem element 23 may be rotated between open and closed conditions. In its open condition, a valve stem port 28 through the wall 27 registers with the open interior of port 29 of a catheter entry portion 30 of the valved manifold assembly 22. In its closed condition, the stem element 23 seals the communication path between the catheter entry portion 30 and the valve housing portion 24. In both positions of the stem element 23, a fluid flow pathway (the open stem interior 26) remains through the stem element 23.

In FIG. 2, the valved manifold assembly 22 is shown in association with a catheter assembly, designated generally 32. A suction control valve, generally 34, may be connected to the proximal end 36 of the assembly 32. A suction catheter 38 is carried within, and is substantially enveloped by, a flexible sheath 40. The distal end 42 of assembly 32 may be connected to the catheter entry portion 30 of the valved manifold assembly 22. The catheter 38 may then be selectively extended through or withdrawn from the catheter entry portion 30. An extended catheter 38 passes through the valve stem port 28 and out through the open stem interior 26 to an extended length beyond distal end 43 of stem element 23. With the catheter 38 withdrawn, the ventilator connection structure 25 may be rotated to close catheter entry portion 30. Aspiration/ventilation may then continue through the open stem interior 26 and ventilator connection end 45.

Figure 3:
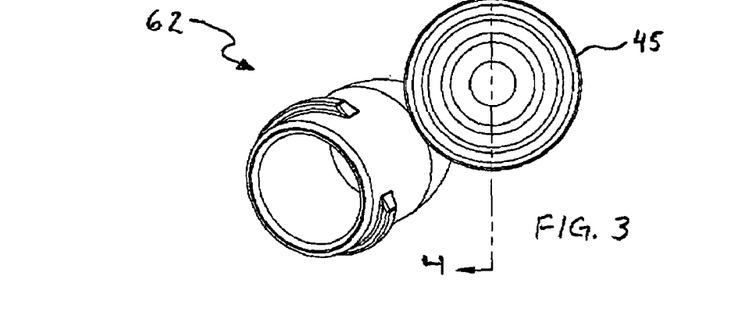
FIG. 3 is a pictorial view of a first valved manifold incorporating the invention, the manifold being shown from its ventilator connection end, with the valve stem rotated approximately 30 degrees from its fully closed condition.

FIG. 3 shows a first valved manifold, designated generally 62, of this invention from its ventilator connection end 45. It is constructed generally the same as the valved manifold assembly 22 of FIG. 1, except for the modifications described in this specification. Accordingly, like numbers are used to designate corresponding like features. The operation of the valved manifold 62 of this invention is substantially as described by the '326 patent, the disclosure of which is incorporated herein by reference to avoid duplication of description.

Figure 4:
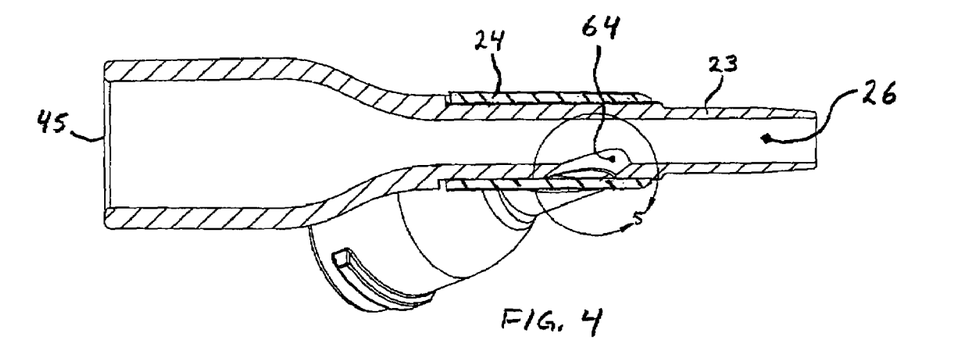
FIG. 4 is a view, partially in section, taken along the section line 4-4 of FIG. 3.
Figure 5:
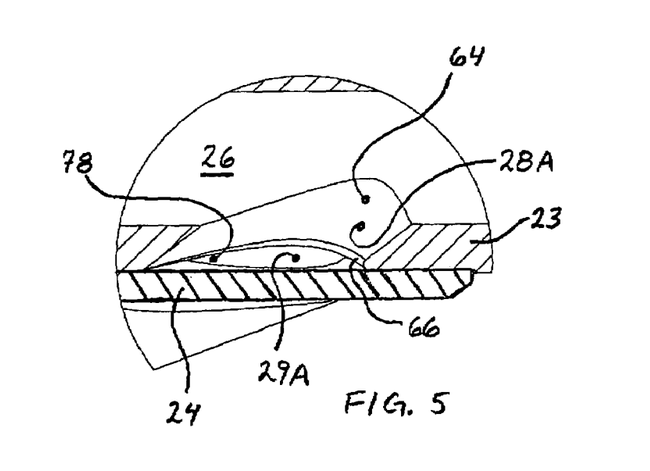
FIG. 5 is an enlarged detail view of the portion of FIG. 4 labeled "5"

FIGS. 4 and 5 show internal features embodying the invention; specifically the size and shape of the pocket 64. Illustrated pocket 64, adapted for a neonatal application, encompasses about 0.001 additional cubic inches of volume. This pocket 64 resides primarily in the stem element 23 at the interface between the stem element 23 and the interior wall of the valve housing portion 24. It is shaped and dimensioned to receive and contain a segment of a catheter (not shown) extended through the open stem interior 26. As the pocket 64 is rotated with the valve stem element 23, the captured segment of a catheter so positioned can be rotated with the valve to approximately the fully closed position without shearing the catheter.

The port 28A is relatively elongate and approximately oval shaped. The modified port 28A and pocket 64 permit a catheter to adjust its local orientation relative to the stem interior 26 to a more enhanced degree than would be possible in port 28 structure of FIG. 1. Such adjustment in local orientation of the catheter reduces a shearing force applied to the catheter by stem element 23 and catheter entry portion 30, compared to the prior art. A valved manifold assembly 22 structured according to the invention includes structure, such as pocket 64, that permits or encourages a catheter to be folded about the body of the valve housing portion 24, thereby reducing damage to the catheter. The pocket 64 can be structured to permit a catheter to rotate in a direction, from an installed neutral position, to reduce the size of its cross-section that must be folded as a valve is closed.

Furthermore, at least a portion of the trailing edge 66 of port 28A desirably is radiused as illustrated in FIG. 5, or otherwise blunted, additionally to change a load applied to a catheter by structure of a closing valve. As modified according to principles of the instant invention, the corner surface of illustrated edge 66 includes a surface having a radius, although such radius need not be a constant value. Radiused edge 66 simply forms a more blunt surface adapted for contact to a catheter sidewall as the valve portion of manifold 62 is displaced in a closing direction. At least a portion of radiused edge 66 presses onto a catheter sidewall in compression as the valve portion of manifold 62 is closed onto the catheter. Such contact with blunt edge 66 tends to crush the catheter, rather than acting like a sharp edge of a pair of scissors and cutting the catheter by way of a substantially pure shear loading. Radiused edge 66 also acts somewhat like a bearing, in that it better slides across a catheter sidewall surface, rather than digging into that surface with the cut-enhancing action of a sharp edge.

Still with reference to FIG. 5, a portion of a cooperating edge of port 29A may also be blunted, further to reduce a shear loading on a catheter as a valve portion is closed. The cooperating edge of port 29A includes that portion which last overlaps the stem structure to form a seal between the catheter entry portion 30 and interior 26 of stem element 23. However, it must be recognized that blunting structure arranged in a mold cavity and operable to blunt a corner/edge portion of port 29A requires a more complex core arrangement to permit removal of molded parts.

In the improvement, the load applied on the trapped catheter is changed from substantially a pure shear load across a diagonally trapped cross-section of the catheter. Contact onto a catheter sidewall by the radiused edge 66 occurs spaced apart in a normal direction from the shear plane substantially defined by the perimeter of port 29A at the cylindrical inner surface of the valve housing portion 24. (Note that the thus-defined shear plane is not a planar geometric element, but is better described as a section of a cylindrical element. In that context, normal may be defined relative to a local portion of such surface). Disposing the contact location of port structure-to-catheter sidewall at a location spaced apart from the shear plane provides a moment arm effective to assist in folding a squashed catheter. The end result is preferentially to deform the catheter, rather than simply cut it by an applied shear load. Consequently, as a practical matter, an attendant attempting to rotate the stem element 23 to its closed condition is more likely to notice resistance well before an emplaced catheter is damaged.

Figure 6:
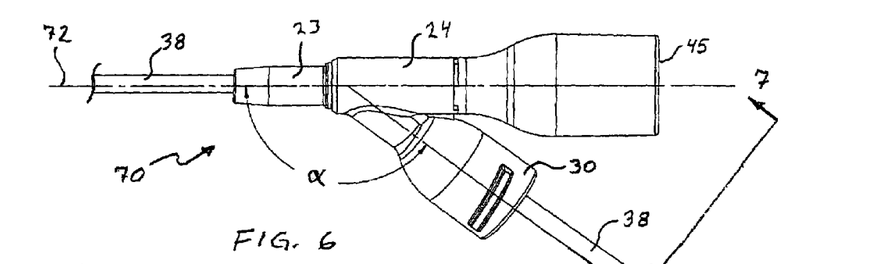
FIG. 6 is a top view of a second valved manifold constructed according to principles of the invention, including a portion of an installed catheter.
Figures 7, 8:
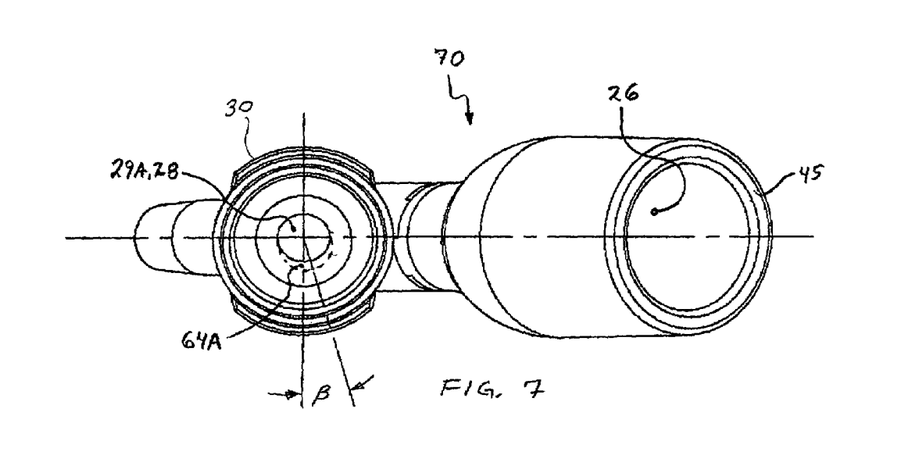
FIG. 7 is a close-up end view in elevation, looking into the opening of the access port of the manifold of FIG. 6 (at section 7-7 and looking in the direction of the arrows), without an installed catheter.
FIG. 8 illustrates a shear-loaded plane located between closing components of both an unmodified valve and one embodiment of a modified valve.
Figure 9:
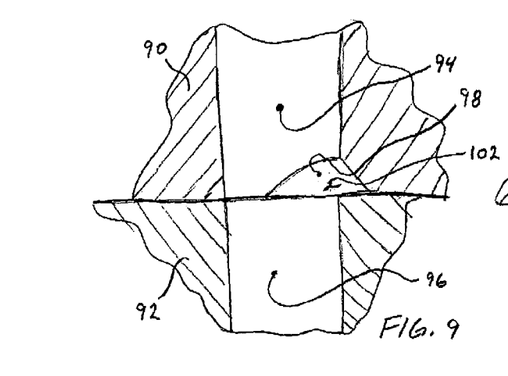
FIGS. 9-12 illustrate planar components arranged to better illustrate certain aspects of the invention.

FIGS. 6 and 7 illustrate a second valved manifold, generally indicated at 70, constructed according to principles of the invention. With reference to FIG. 6, a horizontal plane may be defined containing axis 72 of stem element 23 and axis 74 of catheter entry portion 30. An angle $\alpha$, measured between axis 72 and axis 74, typically is about 142 degrees. Angle $\alpha$ desirably is oblique, whereby to facilitate insertion of a catheter into open interior 26 in stem element 23. A second embodiment of a pocket 64A is formed in the structure of valve housing portion 24 in association with port 29. Illustrated pocket 64A may be substantially defined by a volume removed through a Boolean subtraction operation on wall structure of port 29 of a conventional neonatal catheter that is substantially defined by approximately prismatic shapes adapted to provide a moldability-enhancing draft, and a cutting cylinder having a diameter sized approximately in harmony with a diameter of a catheter, such as catheter 38. As illustrated in FIG. 7, an axis of the cutting cylinder lies in a plane passing through axis 74 and oriented at an angle $\beta$ from a normal to the horizontal plane. It currently is preferred for angle $\beta$ to be about 15 degrees. However, angle $\beta$ may be selected from an operable range between about 5 degrees and about 90 degrees. The combination of angles $\alpha$ and $\beta$ operate in harmony to urge a separation between edge structure of ports 28 and 29, providing a space in which to receive a catheter without shearing through its cross-section.

One effect that certain embodiments of pocket 64A may have on a load applied to an entrapped catheter, which is pinched between edge structure of cooperating ports in a closing valve, can best be described with reference to FIGS. 5 and 8. In a valved manifold assembly 22 having a conventional arrangement of ports 28 and 29, a stress concentration is imposed at a sharp corner area 78 of a cross section 80 at the shear plane of an entrapped catheter. With reference to FIG. 8, illustrated pocket 64A provides an additional area 82 at the shear plane, effective to reduce an average applied stress across that shear plane, compared to the conventional arrangement. Furthermore, a magnitude of the stress concentration at area 78 is reduced, because the effective sharp corner imposed at area 78 by closing edge structure of the valve is reduced in sharpness.

Pocket 64A can effectively change the shape of the catheter's cross-section that is loaded in shear to provide a more uniform cross-section thickness, denoted as "T" in FIG. 8. With illustrated pocket 64A, an effective length, in a direction normal to the thickness "T," of the entrapped cross-section also increases. Because the pocket 64A effectively enlarges an opening of port 29A, valve actuation structure (e.g., stem element 23) must be rotated by an additional increment to fully close the valve. In one currently preferred embodiment of valved manifold 62, stem element 23 must be rotated by about an additional 15 degrees to fully close the opening through port 28A, when compared to an unmodified valved manifold assembly 22 of corresponding size.

FIGS. 9-12 illustrate the principles of operation of the invention in structure having less complexity compared to a valved manifold 62. The structures illustrated in FIGS. 9-12 include flat plates 90 and 92. Plate 90 may be regarded as analogous to a stem element 23, with plate 92 being analogous to a valve housing portion 24. Of course, the reverse may also be equally workable. Plate 90 carries a conduit bore 94 that can be positioned in registration with, for fluid communication through, conduit bore 96 in plate 92. The illustrations depicted in FIGS. 9-12 are cross-sectional views looking at a plane passing though a centerline of the bores 94 and 96, and extending transversely in a direction of "valve" actuation. Bores 94 and 96 are simple orthogonal cylindrical conduit structures. Bore 94 also carries a pocket 98 disposed at an interface between plate 90 and plate 92. Pocket 98 is defined, at least in part, by wall 102.

The wall 102 forming pocket 98 desirably is arranged at an angle relative to a local normal N (see FIG. 12) of the shear plane defined by perimeter edge structure including edge 106 and edge 108. Consequently, a load F applied by wall 102 to the sidewall of an entrapped catheter 110 (see FIGS. 10 and 12) has a component N directed normal to the shear plane, and in addition to the shear component S. "Valve" structures such as illustrated in FIG. 11 and lacking a pocket (such as pocket 98), apply only a load S at the shear plane. A pocket 98 introduces a normal component of load operable to urge edge structure (e.g., edges 106, 108) defining boundaries of the shear plane in opposite directions effective to separate the seal formed between the plates 90 and 92. The separated plates 90, 92 can therefore provide a space in which the squashed catheter 110 may fit as the "valve" is displaced to a fully closed position. Therefore, the entrapped and squashed catheter 110 is more likely to be spared damage to such an extent that it is no longer serviceable.

Figure 12:
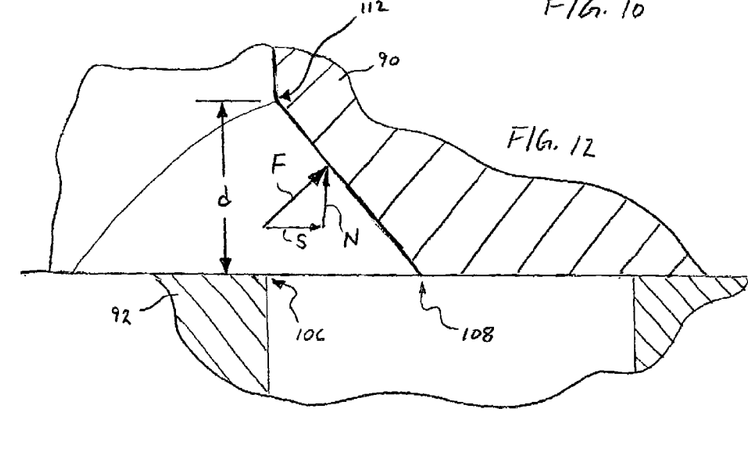

Wall 102 can be flat (chamfered, as illustrated in cross-section), or radiused, or may have any other operable configuration. The wall 102 of pocket 98 resists digging into a trapped catheter sidewall to resist damaging that catheter. The illustrated wall 102 is one embodiment of a blunt trailing edge. When closing a valved manifold 62, an operator may therefore receive additional feedback that a catheter improperly is present, compared to an unmodified valved manifold assembly 22. Wall 102 may be formed to include, or be formed by, a radiused edge 66. In general, a pocket typically provides structure adapted to slide in a catheter's axial direction better than the sharp corner or squared-off boundary edge of corresponding port structure of a prior art valved manifold assembly 22.

Figure 10:
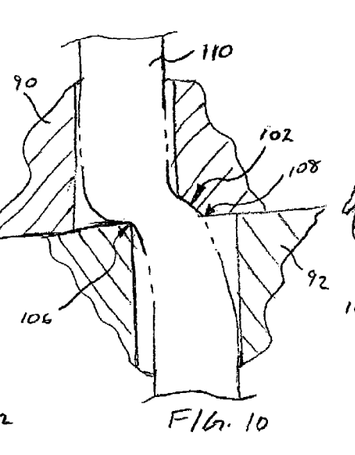
Figure 11:
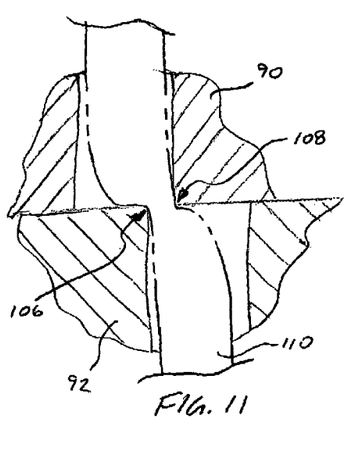

With reference to FIGS. 10 and 12, it may be seen that a portion 112 of the wall 102, which includes the trailing edge 108, is adapted to make contact with a sidewall of catheter 110 at a location spaced apart by a distance "d" in a normal direction from a shear plane formed between plates 90 and 92. The moment generated by the offset distance "d" is operable to urge folding of the catheter 110 with respect to edge 106 as the "valve" structure is displaced towards a closed position.

The stem element 23 and valve housing portion 24 of a valved manifold assembly 22 or valved manifold 62 typically are manufactured by injection molding of medical grade plastic, or similar operable material, inside suitably formed tooling. Tooling used to mold prior art valved manifold assemblies 22 typically employs simple cylindrical cores to define bores 28 and 29. Therefore, valved manifold assembly 22 typically has sharp corners at boundary edges 106 and 108. Such sharp edges are prone to shearing through delicate catheters 110 at the plane defined by edges 106 and 108 when those valve structures are closed onto an entrapped catheter. Sharp, or substantially squared-off, corner edges of prior art devices dig in and apply a substantially pure shear loading S to an entrapped catheter.

Figure 13:
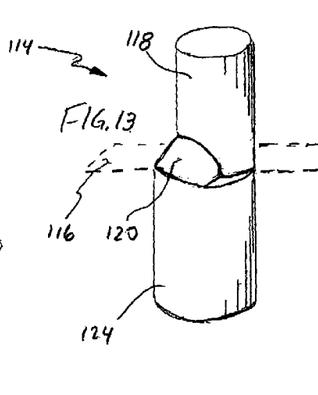
FIG. 13 illustrates a core pin operable to produce a pocket in a molded article according to principles of the invention.

In an improved valve, such as valved manifold 62 illustrated in FIG. 3, an effort typically is made to create tooling that includes a modified mold cavity having core structure adapted directly to form improved structure, such as pocket 64 with a radiused edge 66, or alternatively shaped wall 102. For example, FIG. 13 illustrates a core, generally indicated at 114, operable simultaneously to form both of bore 94 and pocket 98 depicted in FIG. 9. The mold's parting line is illustrated at plane 116. Cylindrical portion 118 is adapted to form bore 94, with pocket 98 being defined by volume addition 120. Cylindrical portion 124 may be carried in sliding reception in a mold cavity to permit removal of a molded article, if required. It is within contemplation alternatively to machine improved pocket structure into valve components structured according to the '326 patent, and made using unmodified tooling.

Reference in this disclosure to details of the illustrated or other preferred embodiments is not intended to limit the scope of the appended claims, which themselves recite those features regarded as important to the invention. Individual structural features may be used alone, or in combination, to form additional embodiments structured according to principles of the invention. For example, alternatives within contemplation may include any or all of: a pocket 64, pocket 64A, and a blunt edge 66.

What is claimed is:

1. In a valved manifold of the type used in a patient ventilation/aspiration system, including a valve comprising a hollow stem defined by an approximately cylindrical sidewall and a first port through said sidewall, said stem being positioned within a valve housing, which openly communicates through a second port with a catheter entry channel in an arrangement permitting said stem to rotate within said housing between a first closed position in which said stem blocks fluid flow through said second port and a second open position in which said first port registers with said second port, whereby a catheter may be inserted through said entry channel and said first port into said hollow stem, an improvement which comprises: a pocket cavity associated with said first port and shaped and dimensioned to accommodate the local rotation of an inserted catheter, as structure of said valve is displaced toward a closed position, such that a wall portion of said catheter is folded over, preferentially to being sheared through by, structure associated with said valve.

2. The improvement according to claim 1, wherein said pocket cavity is configured and arranged to permit said local rotation in a selected direction operable to decrease the size of a cross-section of said catheter operated upon in shear by structure of said valve as said valve is displaced toward said closed position.

3. The improvement according to claim 1, wherein said pocket cavity is configured to permit a catheter to rotate in a selected direction to reduce the size of that cross-section which must be folded as structure of said valve is displaced toward said closed.

4. The improvement according to claim 3, wherein said pocket cavity is configured to permit said rotation to increase alignment of a local axis of said catheter, from a neutral position, with a vector oriented in a valve closing direction at a circumference of said valve housing at said first port.

5. The improvement according to claim 1, wherein said first port comprises a blunt trailing edge.

6. The improvement according to claim 5, wherein a portion of a surface forming said trailing edge is adapted to make contact with a sidewall of said catheter at a location spaced apart in a normal direction from a shear plane formed between components of said valve operably to urge folding of said catheter.

7. The improvement according to claim 5, wherein said blunt trailing edge comprises a radiused surface.

8. The improvement according to claim 5, wherein said trailing edge is configured better to slide transversely under load on a catheter sidewall surface, as compared to a sharp corner.

9. The improvement according to claim 1, wherein said pocket cavity may be substantially defined by a volume removed from a wall structure of a first port of a conventional neonatal catheter that is substantially defined by approximately prismatic shapes adapted to provide a moldability-enhancing draft, and a cutting cylinder having a diameter sized approximately in harmony with a diameter of said catheter, wherein an axis of said cutting cylinder lies in a plane passing through an axis of said first port and oriented at an angle of about 15 degrees from a normal to a plane containing said axis of said first port and an axis of said stem.

10. The improvement according to claim 9, wherein said pocket cavity comprises an additional volume disposed interior to said manifold and about 0.001 cubic inches in size.

11. In a valved manifold of the type used in a neonatal patient ventilation/aspiration system, including a valve comprising a hollow stem defined by an approximately cylindrical sidewall and a first port through said sidewall, said stem being positioned within structure defined by a valve housing, which openly communicates through a second port with a catheter entry channel in an arrangement permitting said stem to rotate within said housing between a first closed position in which said stem blocks fluid flow through said second port and a second open position in which said first port registers with said second port, whereby a catheter may be inserted through said entry channel, said second port and said first port into said hollow stem, an improvement which comprises: a blunt tailing edge associated with said first port and shaped and dimensioned to urge a wall portion of said catheter to fold over, preferentially to being sheared through by, structure associated with said valve.

12. The improvement according to claim 11, wherein a portion of a surface forming said trailing edge is adapted to make contact with a sidewall of said catheter at a location spaced apart in a normal direction from a shear plane operably to urge folding of said catheter.

13. The improvement according to claim 11, wherein said blunt trailing edge comprises a radiused surface.

14. The improvement according to claim 11, wherein said trailing edge is configured better to slide transversely under load on a catheter sidewall surface, as compared to a sharp corner.

15. The improvement according to claim 11, further comprising: a pocket substantially defined by a volume removed from a wall structure of a first port of a conventional neonatal catheter that is substantially defined by approximately prismatic shapes adapted to provide a moldability-enhancing draft, and a cuffing cylinder having a diameter sized approximately in harmony with a diameter of said catheter, wherein an axis of said cutting cylinder lies in a plane passing through an axis of said first port and oriented at an angle of about 15 degrees from a normal to a plane containing said axis of said first port and an axis of said stem.

16. The improvement according to claim 15, wherein said pocket comprises an additional volume disposed interior to said manifold and about 0.001 cubic inches in size.

17. An interface assembly for closed system endotracheal ventilating and aspirating procedures, comprising: a valved manifold having a ventilation port in open communication with an interior chamber; a patient connection port in open communication with said interior chamber and forming a fluid flow path with said ventilation port, said patient connection port being sub stantially in registration with said ventilation port; and an access port in communication with said interior chamber and substantially out of registration with said patient connection port; said access port and said patient connection port being positioned to provide a catheter travel pathway through said access port, a portion of said interior chamber, and said patient connection port, said catheter travel pathway including that portion of the fluid flow path from said interior chamber throughout said patient connection port; and a valve, comprising: a hollow stem having a first port positioned within said catheter travel pathway, said stem being constructed and arranged for movement between a first position in which a wall portion of said stem blocks said catheter travel pathway, and a second position in which said first port and said stem provide a portion of said catheter travel pathway; and actuation structure linked to said stem and operable to move said stem between said first and second positions; said valve further being constructed and arranged to avoid blocking fluid flow through said hollow stem between said ventilation port and said patient connection port; wherein: a pocket cavity is structured and arranged to effect a portion of an entrapped catheter at a shear plane formed by structure of said first port and said second port, as structure of said valve is displaced toward a closed position, such that a wall portion of said catheter is placed into compression between, preferentially to being sheared through by, structure associated with said valve.

18. In a valved manifold of the type used in a patient ventilation/aspiration system, including a valve comprising a hollow stem defined by an approximately cylindrical sidewall and a first port through said sidewall, said stem being positioned within a valve housing, which openly communicates through a second port with a catheter entry channel in an arrangement permitting said stem to rotate within said housing between a first closed position in which said stem blocks fluid flow through said second port and a second open position in which said first port registers with said second port, whereby a catheter may be inserted through said entry channel and said first port into said hollow stem an improvement comprising: a pocket cavity associated with said second port and shaped and dimensioned to permit a wall portion of said catheter to be compressed by, preferentially to being sheared through by, structure associated with said valve as structure of said valve is displaced toward a closed position.

19. The improvement according to claim 18, wherein said pocket cavity is configured and arranged to reduce a magnitude of a shear stress concentration at an edge of a cross-section of an entrapped catheter as said valve is displaced toward a closed position.

20. The improvement according to claim 18, wherein said pocket cavity is configured to enhance uniformity of a width of that cross-section of an entrapped catheter which is pinched between edge structure of said first port and edge structure of said second port as structure of said valve is displaced toward a closed position.

21. The improvement according to claim 20, wherein wall structure of said pocket cavity is configured and arranged to introduce a load component, at a shear plane formed between components of said valve, directed normal to said shear plane and operable to urge said components in a direction effective to separate an air-resistant seal formed between said components.

22. The improvement according to claim 18, wherein said first port comprises a blunt trailing edge.

23. The improvement according to claim 22, wherein a portion of a surface forming said trailing edge is adapted to make contact with a sidewall of said catheter at a location spaced apart in a normal direction from a shear plane formed between components of said valve operably to urge folding of said catheter.

24. The improvement according to claim 22, wherein said blunt trailing edge comprises a radiused surface.

25. The improvement according to claim 22, wherein said trailing edge is configured better to slide transversely under load on a catheter sidewall surface, as compared to a sharp corner.

26. The improvement according to claim 18, wherein said pocket cavity may be substantially defined by a volume removed from a wall structure of said second port in a conventional neonatal catheter that is substantially defined by approximately prismatic shapes adapted to provide a moldability-enhancing draft, and a cutting cylinder having a diameter sized approximately in harmony with a diameter of said catheter, wherein an axis of said cutting cylinder lies in a plane passing through an axis of said second port and oriented at an acute angle from a normal to a plane containing said axis of said second port and an axis of said stem.

27. The improvement according to claim 26, wherein said acute angle is about 15 degrees.

28. The improvement according to claim 26, wherein said pocket cavity comprises an additional volume disposed interior to said manifold and about 0.001 cubic inches in size.

29. In a valved manifold of the type used in a patient ventilation/aspiration system, including a valve comprising a hollow stem defined by an approximately cylindrical sidewall and a first port through said sidewall, said stem being positioned within a valve housing, which openly communicates through a second port with a catheter entry channel in an arrangement permitting said stem to rotate within said housing between a first closed position in which said stem blocks fluid flow through said second port and a second open position in which said first port registers with said second port, whereby a catheter may be inserted through said entry channel and said first port into said hollow stem, an improvement comprising: a pocket disposed in association with an interface between said first port and said second port and adapted to urge folding of an entrapped catheter with respect to an edge of structure at said interface as valve structure is displaced towards a closed position.

30. In a valved manifold of the type used in a patient ventilation/aspiration system, including a valve comprising a hollow stem defined by an approximately cylindrical sidewall and a first port through said sidewall, said stem being positioned within a valve housing, which openly communicates through a second port with a catheter entry channel in an arrangement permitting said stem to rotate within said housing between a first closed position in which said stem blocks fluid flow through said second port and a second open position in which said first port registers with said second port, whereby a catheter may be inserted through said entry channel and said first port into said hollow stem, an improvement comprising: a pocket disposed in association with an interface between said first port and said second port and adapted to resist causing shear-induced damage to an entrapped catheter as valve structure is displaced towards a closed position.

* * * * *